US00PP37101P2

(12) United States Plant Patent
Vermeulen et al.

(10) Patent No.: US PP37,101 P2
(45) Date of Patent: Nov. 18, 2025

(54) ***DRACAENA* PLANT NAMED 'Janet Lindo Gold'**

(50) Latin Name: *Dracaena steudneri*
Varietal Denomination: Janet Lindo Gold

(71) Applicants: Joost Vermeulen, Lubbeek (BE); Mathijs Vermeulen, Lubbeek (BE)

(72) Inventors: Joost Vermeulen, Lubbeek (BE); Mathijs Vermeulen, Lubbeek (BE)

(73) Assignee: Vermeulen NV, Lubbeek (BE)

( * ) Notice: Subject to any disclaimer, the term of this patent is extended or adjusted under 35 U.S.C. 154(b) by 0 days.

(21) Appl. No.: 19/229,603

(22) Filed: Jun. 5, 2025

(51) Int. Cl.
*A01H 5/12* (2018.01)
*A01H 6/12* (2018.01)

(52) U.S. Cl.
USPC ..... Plt./383

(58) Field of Classification Search
USPC ..... Plt./383
See application file for complete search history.

(56) References Cited

U.S. PATENT DOCUMENTS

PP32,804 P2 * 2/2021 Scheffers ..... A01H 6/12
Plt./383

* cited by examiner

*Primary Examiner* — Susan Mccormick Ewoldt
(74) *Attorney, Agent, or Firm* — Samuel R. McCoy, Jr.

(57) ABSTRACT

A new and distinct *Dracaena* plant named 'Janet Lindo Gold' which is characterized by the combination of dark green mature foliage that is very narrowly margined with a golden yellow general coloration, relatively broad and heavily spiraled foliage with coarsely undulate margins, strong plant vigor, resistance to foliage sun scorch, and the stability of these characteristics from generation to generation.

2 Drawing Sheets

Latin name of the genus and species: The Latin name of the genus and species of the novel variety disclosed herein is *Dracaena steudneri*.

Variety denomination: The inventive cultivar of *Dracaena* disclosed herein has been given the variety denomination 'Janet Lindo Gold'.

BACKGROUND OF THE INVENTION

Parentage: 'Janet Lindo Gold' is a spontaneous whole-plant mutation from an unnamed *Dracaena steudneri* (not patented) plant. The inventor is a commercial ornamental plant producer who regularly discovers mutations of *Dracaena* at his greenhouse operation in Lubbeek, Belgium. For said mutations which seem to exhibit commercial potential, cuttings are taken and rooted to produce trial plants which are subsequently grown for evaluation. The variety now called 'Janet Lindo Gold', which was initially discovered in March of 2018, exhibited dark green foliage that was very narrowly margined with a golden yellow coloration relative to the parent which does not possess the golden yellow foliar margin coloration. At the time of discovery, cuttings were taken, and the resulting plants were evaluated at the inventor's greenhouse. After further evaluation, it was determined that the candidate's unique foliage coloration, in combination with strong plant vigor and resistance to foliage sun scorch resulting from over exposure to sunlight, would prove favorable for commercial marketability. Said mutation was isolated for further evaluation to confirm the uniformity and stability of the unique characteristics first observed. Upon confirmation of the stability and uniformity of the characteristics first observed, the new plant was selected for commercialization.

Asexual Reproduction: Asexual reproduction of 'Janet Lindo Gold' is accomplished by way of rooting stem cuttings. Propagation was first performed in 2018 at the inventor's commercial greenhouse in Lubbeek, Belgium. Through seven subsequent generations, the unique features of this cultivar have proven to be stable and true to type.

SUMMARY OF THE INVENTION

The cultivar 'Janet Lindo Gold' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Janet Lindo Gold'. These characteristics in combination distinguish 'Janet Lindo Gold' as a new and distinct *Dracaena fragrans* cultivar:

1. *Dracaena* 'Janet Lindo Gold' exhibits relatively broad, lightly spiraled foliage with coarsely undulate margins born on an unbranched dark yellow-green stem; and
2. *Dracaena* 'Janet Lindo Gold' exhibits juvenile foliage that is colored with a blend of green and yellow-green and very narrowly margined with a translucent greyed-green coloration; and
3. *Dracaena* 'Janet Lindo Gold' exhibits dark green mature foliage with very narrow golden yellow margins; and
4. *Dracaena* 'Janet Lindo Gold' exhibits strong plant vigor and resistance to foliage sun scorch resulting from overexposure to sunlight.

BOTANICAL DESCRIPTION OF THE PLANT

Figure 1:
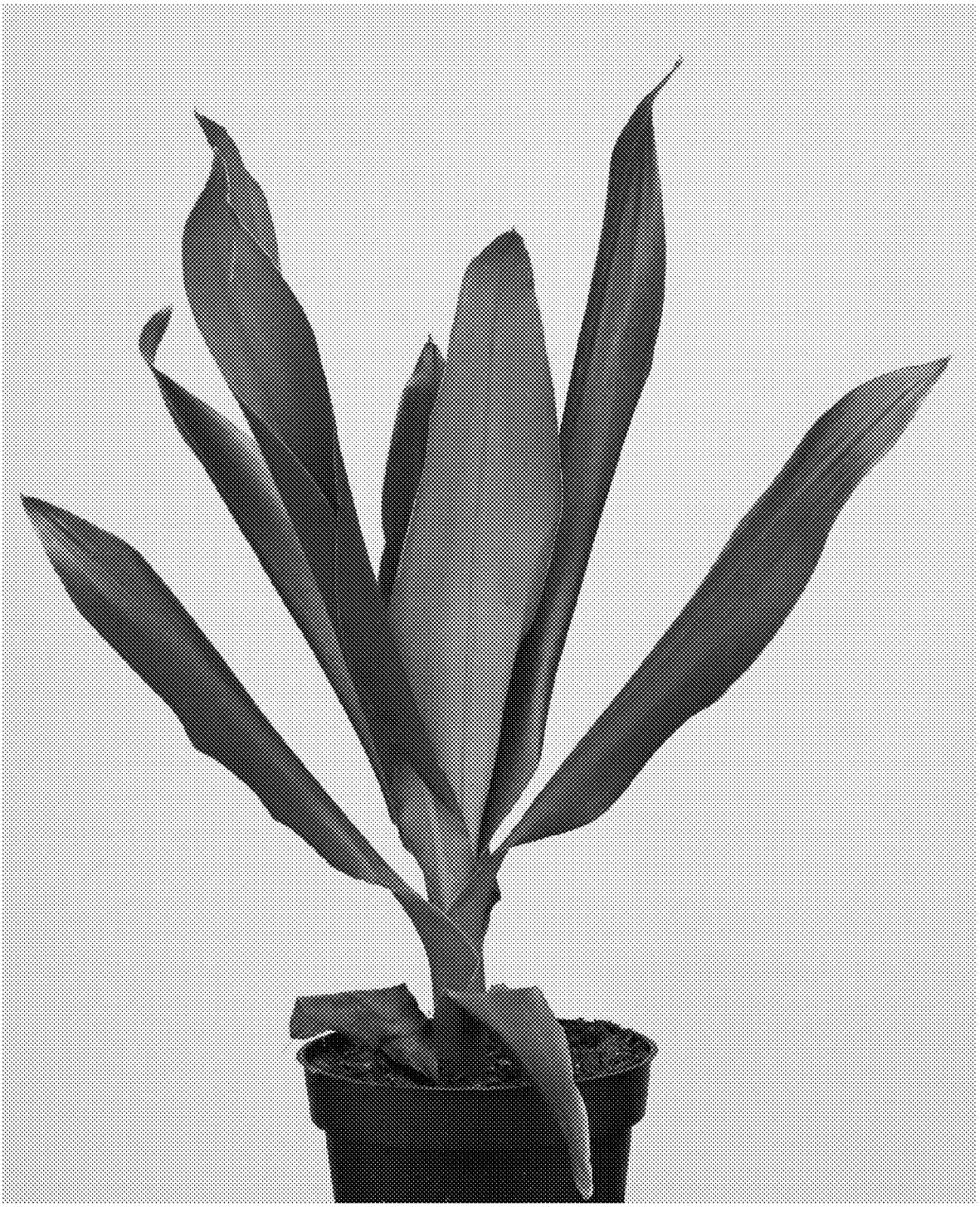
FIG. 1 illustrates, as nearly true as it is reasonably possible to make the same in color photographs of this type, an exemplary plant of 'Janet Lindo Gold' grown in Lubbeek, Belgium. This plant, grown in a 11 cm nursery container, is approximately 26-weeks-old from a rooted young plant.
Figure 2:
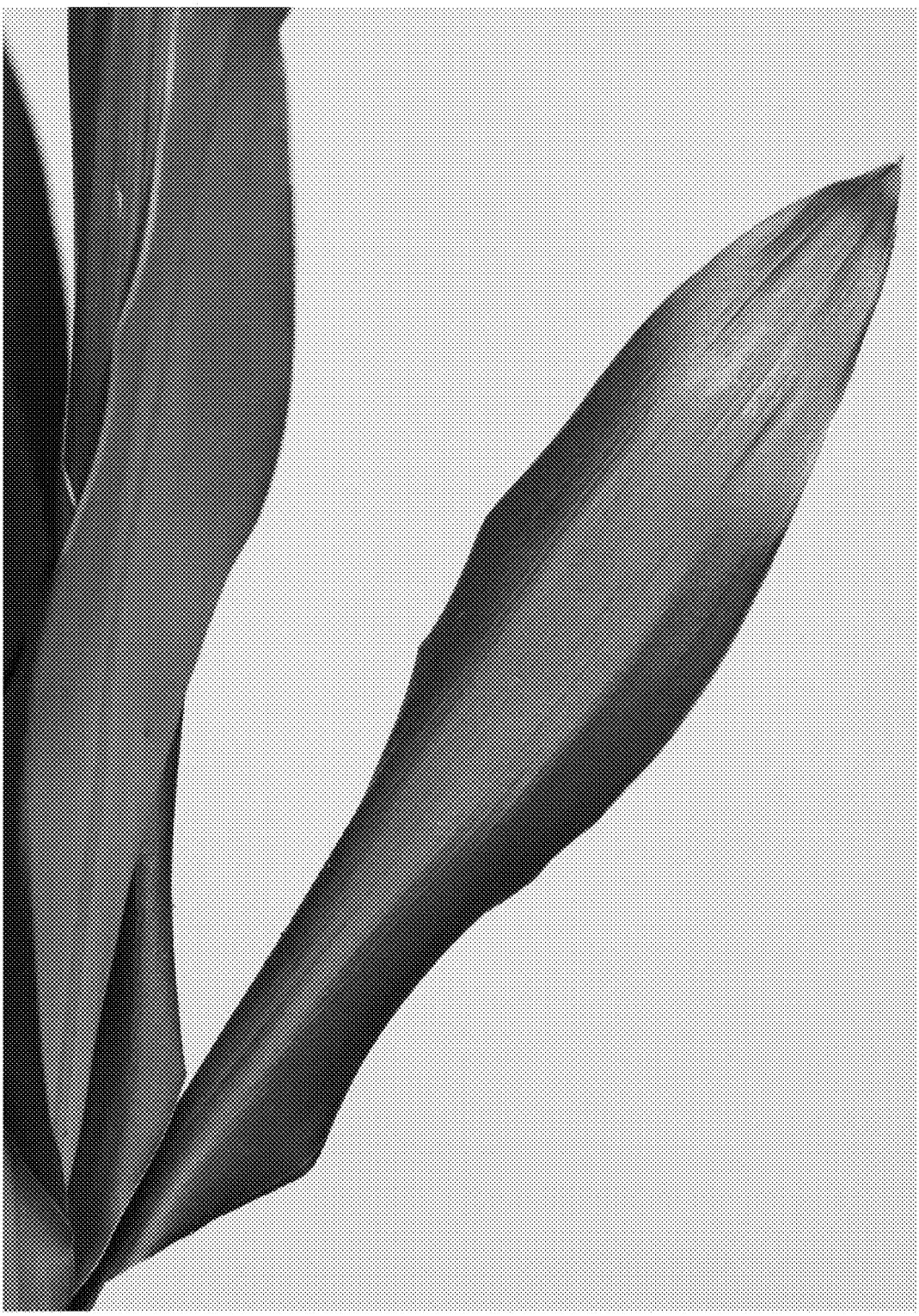
FIG. 2 illustrates, as nearly true as it is reasonably possible to make the same in color photographs of this type, the typical foliage of 'Janet Lindo Gold'.

The following observations and measurements, made in December of 2024, describe averages from a sample set of six specimens of 26-week-old 'Janet Lindo Gold' plants grown in 11 cm nursery pots in Lubbeek, Belgium. Plants were produced using conventional greenhouse production protocols for *Dracaena* sp. which consisted of growing under 70% shade, overhead irrigation at regular intervals, and fertigation.

Those skilled in the art will appreciate that certain characteristics will vary with older or, conversely, with younger plants. 'Janet Lindo Gold' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, Sixth Edition.

A botanical description of 'Janet Lindo Gold' and comparisons with the parent plant and most similar commercial *Dracaena* cultivar known to the inventor are provided below.

Plant description:

*Growth habit*.—Upright evergreen perennial with foliage born on a solitary unbranched stem.

*Plant profile*.—Broad obovate.

*Average height from base to top of foliage*.—34.0 cm.

*Average width*.—30.2 cm.

*Propagation details*.—Asexual propagation is accomplished by stem cuttings.

*Time to initiate roots*.—Approximately 21 weeks are required to initiate roots at 20 degrees Celsius.

*Time to produce a marketable* 11 *cm potted plant*.—Approximately 26 weeks. Pinching will increase lateral branching.

*Disease and pest resistance or susceptibility*.—Neither tolerance nor resistance to normal diseases and pests of *Dracaena fragrans* have been observed.

*Environmental tolerances*.—Adapt to USDA Hardiness Zones 10 through 12 and temperatures as high as 40 degrees Celsius; moderate tolerance to rain and wind.

Root system:

*General*.—Fibrous; freely branched and moderately dense rooting.

*Distribution in the soil profile*.—Shallow to moderately deep.

*Texture*.—Smooth; glabrous.

*Color*.—Greyed-orange, RHS N170A.

Stems:

*Branching characteristics*.—Not freely branched in nature; develops lateral branches only when manipulated by man by way of pruning. Naturally produces one main stem arising from the plant's base.

*Attitude*.—Near vertical.

*Strength*.—Very strong.

*Length*.—12.4 cm.

*Diameter*.—Average 1.0 cm.

*Internode length*.—Average 1.2 cm.

*Stem texture*.—Glabrous; smooth.

*Stem luster*.—Very slightly glossy.

*Color, developing stems*.—Yellow-green, nearest to RHS 145D.

*Color, mature stems*.—Yellow-green, nearest to RHS 145B, with irregularly shaped blotches of green, nearest to RHS 143A.

*Color at the internodes*.—Yellow-green, nearest to RHS 145A.

Foliage:

*Arrangement*.—Alternately spiraled.

*Attachment*.—Sheathed.

*Division*.—Simple.

*Attitude*.—Foliage near the apex is upright to outward and becomes progressively more relaxed towards the base.

*Number of leaves per lateral branch*.—16.

*Lamina*.—Dimensions — 28.8 cm long and 5.6 cm wide, on average. Shape — Lanceolate. Aspect — Very lightly spiraled, with the distalmost portion on the lamina curling downward at an average angle of minus −30 degrees to the rest of the lamina. Apex — Narrowly acute with a mucronate tip. Base — Sheathed. Sheath — Length — 3.3 cm. Width — 2.4 cm. Color, adaxial surface — Green-white, nearest to a blend of RHS 157B and 157C. Color, abaxial surface — Yellow-green, nearest to RHS 145C.

*Margin*.—Entire; coarsely undulate.

*Texture and luster of adaxial surface*.—Smooth, glabrous and moderately glossy.

*Texture and luster of abaxial surface*.—Smooth, glabrous and very slightly glossy.

*Color*.—Juvenile foliage, adaxial surface — Green to yellow-green, nearest to a blend of RHS 143A and 144A; narrowly edged translucent greyed-green, nearest to RHS 192A. Juvenile foliage, abaxial surface — Yellow-green, nearest to RHS 147D; narrowly edged translucent greyed-green, nearest to RHS 192A. Mature foliage, adaxial surface — Green to yellow-green, nearest to a combination of RHS NN137A and 147A; narrowly edged translucent yellow-green, nearest to RHS 150D, generally appearing as a golden yellow coloration. Mature foliage, abaxial surface — Green, nearest to a combination of RHS 137C and 138A; narrowly edged translucent yellow-green, nearest to RHS 150D, generally appearing as a golden yellow coloration.

*Venation*.—Pattern — Parallel. Color, adaxial surface — The midrib is green, nearest to RHS NN137D; lateral veins are green, nearest to a combination of RHS NN137A and 147A. Color, abaxial surface — The midrib is green, nearest to RHS 138B; lateral veins are green, nearest to a combination of RHS 137C and 138A.

Inflorescence: To date, flowering has not been observed.

Seed and fruit: To date, flowering has not been observed.

COMPARISONS WITH THE PARENT PLANT AND CLOSEST KNOWN COMMERCIAL VARIETY

Plants of the new cultivar 'Janet Lindo Gold' may be distinguished from its parent, an unnamed *Dracaena steudneri* plant (not patented) which typifies the species, by the characteristics described in Table 1.

TABLE 1

Comparison between 'Janet Lindo Gold' and The Parent Plant.

| Characteristic | 'Janet Lindo Gold' | The Parent Plant |
|---|---|---|
| Growth habit. | More compact than the parent plant. | Less compact than 'Janet Lindo Gold'. |
| Foliage attitude. | Foliage is generally morer elaxed than the parent plant. | Foliage is generally more upright than 'Janet Lindo Gold'. |
| Foliage aspect. | More spiraled (i.e. axially twisted) than the parent plant. | Less spiralled than 'Janet Lindo Gold'. |
| Foliage margins. | More undulated than the parent plant. | Less undulated than 'Janet Lindo Gold'. |
| General coloration of the mature foliage. | Dark green and very narrowly margined with a golden yellow coloration. | Homogenously dark green; foliar margins are dark green. |

Plants of the new cultivar 'Janet Lindo Gold' may be distinguished from the closest known commercial comparator, *Dracaena fragrans* 'DRAGREYE' (U.S. Plant Pat. No. 32,804), by the characteristics described in Table 2.

TABLE 2

Comparison Between 'Janet Lindo Gold' and 'DRAGREYE'

| Characteristic | 'Janet Lindo Gold' | 'DRAGREYE' |
|---|---|---|
| Foliage attitude and general profile. | Foliage is generally more upright grown on a tall main branch and coarsely undulated to axially spiral. | Foliage is generally more relaxed in a globular shape with basal branching. |
| Plant size. | On average, 34.0 cm in height and 30.2 cm in width; less compact than 'DRAGREYE'. | On average, 14.7 cm in height and 23.4 cm in width; more compact than 'Janet Lindo Gold'. |
| Foliage size. | Larger than 'DRAGREYE'. | Smaller than 'Janet Lindo Gold'. |
| Foliage shape. | Lanceolate. | Lorate. |
| General coloration of the mature foliage. | Dark green and very narrowly margined with a golden yellow coloration. | Green foliage with broad, light green to light yellow axial striations and margins. |

That which is claimed is:

1. A new and distinct cultivar of *Dracaena steudneri* plant named 'Janet Lindo Gold', substantially as described and illustrated herein.

* * * * *